United States Patent [19]

D'Angelo et al.

[11] 4,304,882

[45] Dec. 8, 1981

[54] POLYMER FROM PEROXY COMPOUNDS CONTAINING ACYLATING GROUPS

[75] Inventors: Antonio J. D'Angelo, Englishtown, N.J.; Orville L. Mageli, Kenmore, N.Y.

[73] Assignee: Pennwalt Corporation, Philadelphia, Pa.

[21] Appl. No.: 211,093

[22] Filed: Dec. 22, 1971

Related U.S. Application Data

[63] Continuation-in-part of Ser. No. 727,323, May 7, 1968, Pat. No. 3,671,651, which is a continuation-in-part of Ser. No. 285,857, Jun. 6, 1963.

[51] Int. Cl.$^3$ ................................................ C08F 8/10
[52] U.S. Cl. ...................................... 525/98; 525/334; 525/387; 525/61; 525/353; 528/273; 528/370; 260/17.4 GC; 525/96; 525/437; 525/419; 536/56; 568/563; 568/566
[58] Field of Search ................... 260/94.7 A, 877, 879, 260/79.3 R, 75 T, 2 EP; 526/227, 228, 9; 568/563, 566; 536/56

[56] References Cited

U.S. PATENT DOCUMENTS

| | | | |
|---|---|---|---|
| 3,165,546 | 1/1965 | Merrill | 260/502 R |
| 3,433,825 | 3/1969 | Maltha et al. | 526/228 |
| 3,652,520 | 3/1972 | Ryan et al. | 260/94.7 A |
| 3,652,724 | 3/1972 | Shimomura et al. | 260/94.7 |
| 3,671,651 | 6/1972 | D'Angelo | 260/94.2 R |
| 3,671,651 | 6/1972 | D'Angelo | 260/75 T |

OTHER PUBLICATIONS

Taylor, Reactions and Symbols of Carbon Compounds Century Co., New York (1930).

*Primary Examiner*—Joseph L. Schofer

[57] ABSTRACT

Polymers of the formula $[(A_{n1}\text{-R-}D_{n2})_vP_{n3}]_wZ_{n4}$ where A is a peroxy-containing group; R is a 2–4 valent aliphatic, cycloaliphatic or aromatic radical; P is a polyvalent polymeric residue; D is a carbonyl-containing connecting group; and Z is a terminal group, such polymers being useful with vinyl monomers in the formation of block and graft polymers.

9 Claims, No Drawings

POLYMER FROM PEROXY COMPOUNDS CONTAINING ACYLATING GROUPS

CROSS-REFERENCE TO RELATED APPLICATIONS

This is a continuation-in-part of copending application Ser. No. 727,323, filed May 7, 1968 (now U.S. Pat. No. 3,671,651 issued June 20, 1972), which in turn is a continuation-in-part of copending application Ser. No. 285,857, filed June 6, 1963.

BACKGROUND OF THE INVENTION

This invention relates to novel compounds having both a peroxy group and an acylating function and to polymers having at least one peroxy group. Also the invention relates to methods for preparing compounds having both a peroxy group and an acylating function. Also the invention relates to a method of making block and graft polymers from vinyl-type monomers.

THE PRIOR ART

Aliphatic t-alkyl peroxy chloroformate and di-t-alkyl and aralkyl peroxides containing acylating groups are known. A. G. Davies et al, J. Chem. Soc. (1953) p 1808 et seq. prepared aliphatic t-alkyl peroxy chloroformates, such as,

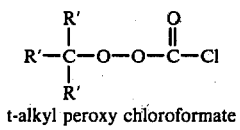

t-alkyl peroxy chloroformate by reacting t-alkyl hydroperoxide with phosgene. The following derivatives were also prepared by reaction of the

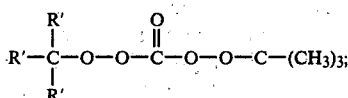

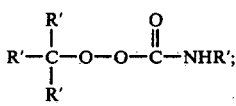

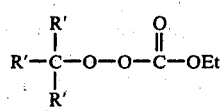

chloroformate with t-butyl hydroperoxide, amines and alcohols. (This type of peroxy compounds containing acylating groups do not fall within the scope of our invention because the peroxy group is not separated from the chloroformyl group and actually is a part of it.)

The di-t-alkyl peroxides containing acylating groups represented by the following structures

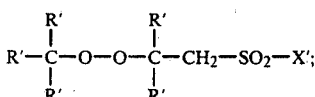

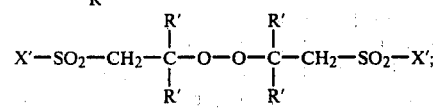

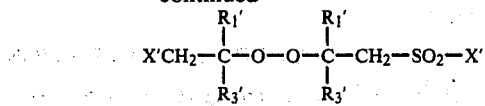

where $R'_1$ and $R'$ are alkyl radicals, $R'_3$ is lower alkyl or aromatic radical, $X'$ is either Cl or Br were prepared in U.S. Pat. No. 2,519,403. Derivatives prepared from the above structures were obtained by replacement of the halogen in $—SO_2—X'$ group with hydroperoxides, alcohols, ammonia, primary and secondary amines in U.S. Pat. No. 2,542,578. (These compounds do not fall within the scope of this invention because the connecting link is $—SO_2—$ rather than

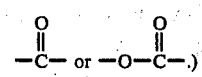

Di-t-aralkyl peroxides containing as acylating groups

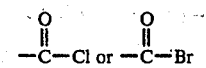

represented by the following structure:

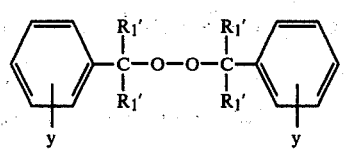

where $R'_1$ is the same or different alkyl radical and y is

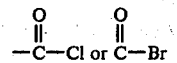

group were prepared in U.S. Pat. No. 3,165,546.

The above phenoxy compounds do not come within this invention. They have many disadvantages:

(1) They are too thermally stable to be useful for vinyl polymerization.

(2) When reacted with polymers containing more than two functional groups, the polymer obtained is a crosslinked one which is not useful for block and graft work due to the inherent insolubility of crosslinked polymer in most organic solvents.

(3) They can only be used in condensation reaction to prepare polyesters, polyamides, etc. and even in applications such as these, the resultant polymer, in order to be useful for block and graft work, an outside source of radiation has to be used in order to decompose the peroxide.

(4) They do not offer a wide range of operating temperature which is so important when working with the preparation of graft and block copolymers from different vinyl monomers.

With peroxidic materials one of ordinary skill in the art would not use the reaction conditions necessary to convert any peroxy compound containing carboxylic or alcohol groups to the desired corresponding acid halide, anhydride and chloroformate. He would expect decomposition of the peroxide to take place especially with peroxides of the diketals, perester, and diacyl type.

SUMMARY OF THE INVENTION

I. A polymer, containing at least one peroxide group, having the formula:

$$[(A_{n1}-R-D_{n2})_v P_{n3}]_w Z_{n4} \qquad (II)$$

where:

(1) A is a peroxy-containing group selected from

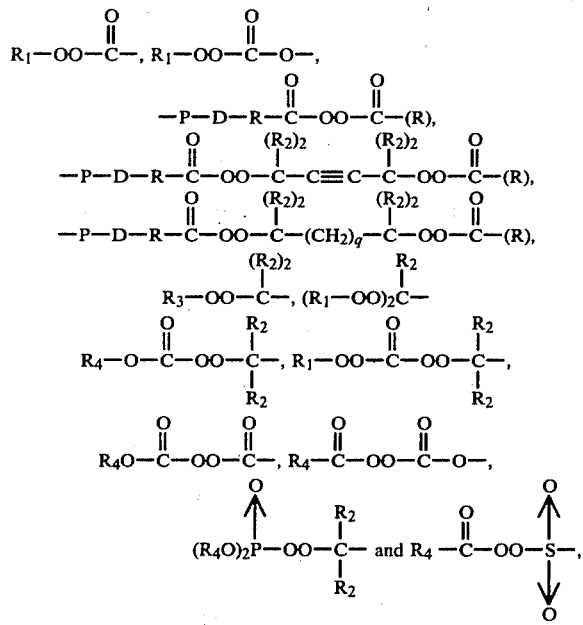

where "(R)" shows the relationship of the A diradicals to R in formula (II);

(2) D is a carbonyl-containing connecting group selected from

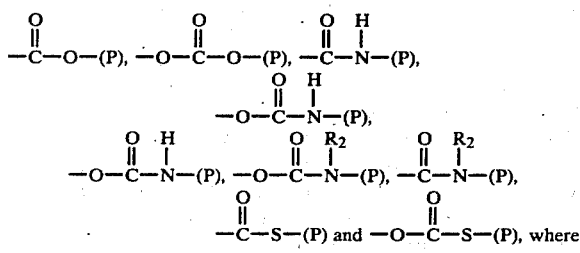

"(P)" shows the relationship of D to P;

(3) P is a polyvalent polymeric residue such as a polyether, polyester, polyamide, polycarbonate, polybutadiene, polystyrene, poly(vinyl alcohol), partially hydrolyzed poly(vinyl acetate), cellulose or a polystyrene-polybutadiene copolymer, P being divalent when A is a diradical or $n_2$ is 2;

(4) Z is selected from —H, —OH, —NH$_2$, —NHR$_2$, —SH, —OR$_2$,

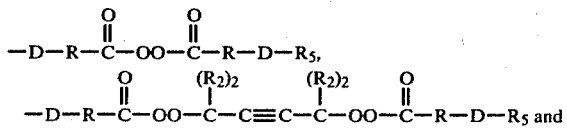

(5) v and w are integers equal to 1–100;

(6) $n_1$, $n_2$, $n_3$ and $n_4$ are integers equal to 1–2;

(7) q is an integer equal to 2–4;

(8) R is a di-, tri- or tetravalent radical selected from alkyl 1–12 carbons, alkenyl of 2–12 carbons, cycloalkyl of 3–8 carbons, or aryl of 6–12 carbons;

(9) R$_1$ is tertiary alkyl of 4–8 carbons;

(10) R$_2$ is alkyl of 1–12 carbons;

(11) R$_3$ is selected from tertiary alkyl of 4–10 carbons and tertiary aralkyl of 9–10 carbons;

(12) R$_4$ is selected from alkyl of 1–12 carbons or aryl of 6–12 carbons; and

(13) R$_5$ is alkyl of 1–4 carbons or hydrogen.

II. The invention includes a method of preparing block and graft polymers by reacting a vinyl-type monomer with polymer II under conditions to decompose the peroxide. Example: A block polymer is prepared by forming a styrene solution, 15 parts by weight, and the polymer product of hydroxyl terminated polybutadiene and bis(4-chloroformylbutyryl) peroxide, 5 parts by weight, and heating said mixture for about 7 hours at 70° C.–100° C., under an inert atmosphere.

DESCRIPTION OF THE INVENTION AND EXAMPLES

Compounds I are peroxy compounds containing a haloformate group or an acid halide group as described in U.S. Pat. Nos. 3,671,651 and 3,952,041, which U.S. Patents are herein incorporated by reference. Compounds I can be reacted with polymeric materials containing terminal or pendant hydroxyl, amino, and mercapto groups or any other functionality that can be acylated. (Examples I, II, III, IV). Compounds containing two acylating groups can be reacted with difunctional monomers to obtain condensation polymers like: polyester, polyamides, etc. (Example VI) containing intermittant peroxy groups along the polymer backbone.

POLYMERS II

In the polymers II as defined above, "Z" is a terminal of pendant group normally selected from —H, —OH, —NH$_2$, —NHR$_2$, —SH or —OR$_2$ (i.e., the terminal group of the starting polymer). However, some of the terminal groups may react with the peroxide compound I to give peroxide-containing end groups, depending on whether the polymer or peroxide reactant is used in excess.

P is a polyvalent polymeric residue such as a polyether, polyester, polyamide, polycarbonate, polybutadiene, polystyrene, poly(vinyl alcohol), partially hydrolyzed poly(vinyl acetate), cellulose, polybutadiene-polystyrene copolymer, and any other polymeric material. More specifically polyether containing aliphatic, cycloaliphatic, aromatic, and heterocyclic diradicals linked to the oxygen atoms; polyester, such as prepared from aliphatic, cycloaliphatic, aromtic, and heterocyclic dibasic acids and dihydroxy compounds; polyamide, such as prepared from aliphatic, cycloaliphatic, aromatic, and heterocyclic dibasic acids and diamines; polycarbonate, such as prepared from aliphatic, cycloaliphatic, aromatic, and heterocyclic dihydroxy compounds and phosgene or aliphatic, cycloaliphatic, aromatic and heterocyclic bis(chloroformates).

Polymer II can be prepared by reaction with polymeric materials containing terminal or pendant hydroxyl, amino, and mercapto groups or any other functionality that can be acylated. Preparations are illustrated by Examples I, II, III, and IV. Polymers II can be used to prepare graft and block polymers with vinyl monomers by decomposing the peroxide present in the polymer (Example VII, VIII, IX, XI).

Polymers II can be used in making graft and block polymers. These block and graft copolymers are useful as compatibilizing agents. The great majority of homopolymers are incompatible with each other. However, when block and/or graft copolymers of two incompatible homopolymers are present, the system becomes much more, if not completely, compatibilized (see Examples VIII and IX).

III. Method of Preparing Block and Graft Polymers

These novel peroxy containing polymers II can be used to make block and graft copolymers by treating them with polymerizable vinyl-type monomers under conditions where the peroxy-carbon linkage is decomposed (ruptured) into free radicals at a rate and temperature suitable for polymerizing the vinyl monomer itself. Suitable vinyl-type monomers include: styrene, butadiene, isoprene, acrylonitrile, vinyl chloride, ethyl acrylate, methyl methacrylate, vinyl acetate, acrylic acid, vinyl stearate, vinylidene chloride, and the like.

Any of the conventional procedures for decomposing the peroxide, such as heating to the proper temperature, activation with amines or transition metal salts, and ultra violet irradiation can be used.

Illustrative block and graft polymers are prepared in Examples VII, VIII, IX and XI.

It is known that when two different polymers are brought in solution—really a dispersion because of the low solubility of polymer in the common organic solvents—in a common solvent, over a period of time the solution segregates into two layers, having different polymeric compositions. Apparently homogeneous melts of two different polymers frequently on solidifying show undesired segregation or heterogeneous dispersion of one polymer throughout the continuous phase of the other polymer. Since physical mixtures (dispersion) of two different polymers afford very desirable physical properties, if a homogeneous mass is maintained, stability of the dispersion is of importance. A "third" component of the mix which improves the dispersion stability of the mix is known as a stabilizer—in certain special areas, the stabilizer is referred as a compatibility agent.

The ability to stabilize is tested in the laboratory by empirical tests where the "stabilized" solution is compared to a control solution. The time for the appearance of two distinct layers is measured. It is to be emphasized that the results cannot be used to compare effectiveness in different polymeric systems, since even polymer molecular weight can cause substantial changes in separation time between two systems made from the same monomers. However the laboratory tests are meaningful in terms of screening potential stabilizers.

An important utility of the block and graft polymers made by the method of the invention is as stabilizers (compatibilizers) of solutions of different homopolymers. This utility is demonstrated by Examples VIII and IX.

Polymers of the invention and the utility of certain compounds of the invention is illustrated by the following working examples:

EXAMPLE I

Reaction of cellulose with 2-(t-butylperoxycarbonyl)-ethyl chloroformate 2.5 g. of cellulose powder (Fisher filtration accelerator NO 9-906) was treated with 20 ml. of sodium hydroxide (50%) and allowed to stand overnight.

The following day the mixture was filtered and the solid suspended in water and reacted with 4 g. of 2-(t-butylperoxycarbonyl) ethyl chloroformate and allowed to stir for 24 hours at +40° C. to +100° C. but preferably at +40° C. to +50° C. After this time the mixture was filtered and the solid washed with benzene and diethyl ether and air dried.

A solid (5 g.) was obtained containing 0.12% A(O).

SPI exotherm in polyester resin at 115° C. and 1% concentration gave the following:
Gel Time in minutes: 7.2
Cure Time in minutes: 11.9
Peak in °F.: 313°

EXAMPLE II

Reaction of hydroxyl-terminated polybutadiene with 2-(t-butylperoxycarbonyl)-ethyl chloroformate

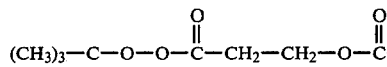 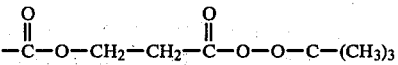

To a mixture of 17.6 g. of hydroxyl-terminated polybutadiene liquid resin (Sinclair R-15 M resin equivalent weight=1330, containing 0.75 meq. OH per gram), diethyl ether and triethylamine (1.4 g. 0.0132 moles) was added a solution of 2-(t-butylperoxycarbonyl)-ethyl chloroformate (3.8 g. of 90% product, 0.0132 moles) in diethyl ether. The mixture was reacted for four hours at +20° C. to +100° C. but preferably at +20° C. to +40° C.

After filtration of the triethylamine hydrochloride and evaporation of the solvent a viscous liquid was obtained (14 g.) that contained 0.91% A(O).

SPI exotherm in polyester resin at 115° C. and 2% concentration gave the following:
Gel Time in Minutes: 5.4
Cure Time in Minutes: 7.5
Peak in °F.: 428°

In the above structure, A is $(CH_3)_3C-OO-C(O)-$; R is $-(CH_2)_2-$; D is $-O-C(O)-O-$; P is polybutadiene; Z is $-H$; $n_1$, $n_2$, $n_3$, $n_4$ and w are 1; and v is 2.

EXAMPLE III

Reaction of hydroxyl terminated polybutadiene with t-butyl o(chloroformyl)peroxybenzoate

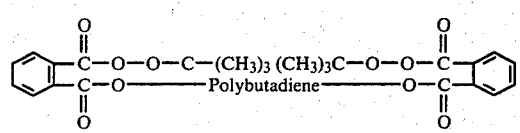

To a solution of 17.6 g. of hydroxy-terminated polybutadiene liquid resin (equivalent weight 1330 g. containing 0.75 meq/g) and triethylamine (1.4 g. 0.0132 moles) in diethyl ether was added a solution of t-butyl o-(chloroformyl)peroxybenzoate (0.0132 moles) in benzene.

After filtration of the triethylamine hydrochloride and evaporation of the solvent a viscous liquid was obtained (16 g.) that contained 0.27% A(O).

SPI exotherm in polyester resin at 115° C. and 2% concentration gave the following:
Gel Time in minutes: 15.1
Cure Time in minutes: 22.0
Peak in °F.: 332°

EXAMPLE IV

Preparation of polyether containing an acylperoxy group

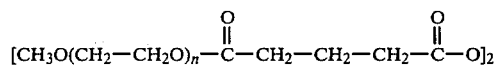

To a solution of 15 g. (0.02 moles) of a monohydroxyl-terminated polyether (Union Carbide Carbowax-750, molecular weight 715–785) and 2.02 g. (0.02 moles) triethylamine in diethyl ether was added a solution of 3.2 g. (0.01 moles) of bis 4-(chloro formyl) butyryl peroxide in benzene.

The mixture was allowed to stir for six hours.

After filtration of the triethylamine hydrochloride, the ether solution was evaporated under reduced pressure.

A viscous liquid was obtained (16 g.) containing 0.54% A(O).

n is 15–17 in the product formula.

EXAMPLE V

Reaction of hydroxyl-terminated polybutadiene with bis(4-chloroformylbutyryl)peroxide in presence of ethanol

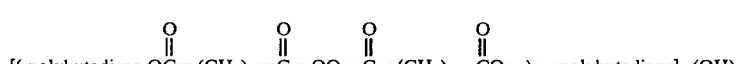

To a solution of 35.2 g. of hydroxyl-terminated polybutadiene (Sinclair R-15 M resin) and 2 g. (0.0264 moles) of triethylamine in diethyl ether was added a solution of bis(4-chloroformylbutyryl) peroxide (96.7%) (4.7 g. 0.0132 moles) in diethyl ether.

After the addition was completed, absolute ethanol was added (1.2 g. 0.0264 moles). The mixture was reacted for two hours. After filtration of the triethylamine hydrochloride, the ether solution was evaporated under reduced pressure. A viscous liquid was obtained (37 g.) containing 0.30% A(O).

v is greater than 1 (but less than 100) in the product formula.

If excess peroxide is used, the end (Z) groups will be peroxidic groups

EXAMPLE VI

Preparation of polyester containing peroxide

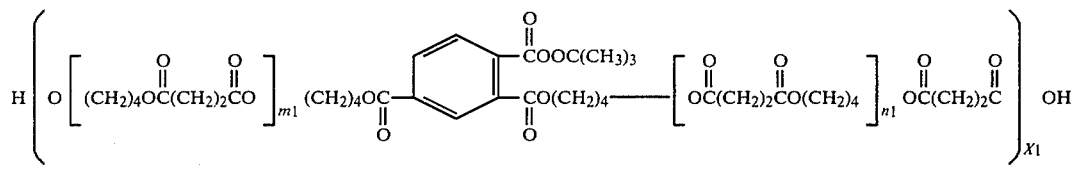

To 2.7 g. (0.03 moles) of 1,4-butanediol and 7.5 g. (0.075 moles) of triethylamine dissolved in diethyl ether was added a solution of 1.9 g. (0.005 moles) t-butyl 2,4(5)-(dichloroformyl)peroxybenzoate and 3.9 g. (0.025 moles) of succinoyl dichloride in benzene.

After filtration of the triethylamine hydrochloride, the organic phase was stripped under vacuum. A viscous residue was obtained. SPI exotherm in polyester resin at 115° C. and 1% concentration gave the following:
Gel Time in minutes: 4.1
Cure Time in minutes: 6.5
Peak in °F.: 385°

"$m_1$, $n_1$, and $X_1$" are each equal to more than 1 in the general formula shown for the polyester product.

EXAMPLE VII

Preparation of block copolymer with styrene from product prepared in Example I

Cellulose(polystyrene)$_{n1}$

To 15 ml. of styrene placed in a tube was added 0.5 g. of the product prepared in Example I. The tube was sealed under an atmosphere of nitrogen and heated for six hours at +60° C. to +100° C.

The reaction product was then extracted with chloroform for 24 hours then dried under vacuum at 50° C. for six hours.

The block copolymer formation was confirmed by pyrolysis analysis with Vapor Phase Chromatography (Perkin-Elmer 154 model). The cellulose containing peroxide (Example I) was pyrolyzed and the gases passed through a 6 ft. column of diisodecyl phthalate ($10^3$ low 4X). The chromatogram showed peaks at 1.75; 1.85; 1.95; and 2.25 minutes.

Similarly polystyrene was pyrolyzed. The chromatogram showed peaks at 1.8; 3.4; 4.7; and to a major peak between at 9.3 and 10.3 minutes.

The prepared block copolymer was also pyrolyzed. From the peaks obtained in this chromatogram (1.75; 1.85; 1.95; 2.25; 3.4 and a peak between 9.3 and 9.75 minutes) one concludes that the block copolymer contained cellulose and styrene.

In order to assure that the chloroform extraction was satisfactory, polystyrene was polymerized in presence of cellulose with AIBN azo-bis(isobutyrylnitrile). The polymer obtained, after extraction with chloroform for 24 hours, was pyrolyzed and analyzed by Vapor Phase Chromatography. No polystyrene peaks could be observed in this polymeric material after the extraction indicating that the extraction technique was satisfactory.

EXAMPLE VIII

Preparation of block copolymer with styrene from product obtained in Example IV

Polyether-Polystyrene

To 15 g. of styrene placed in a tube is added 5 g. of the product obtained on Example IV. The tube is sealed under a nitrogen atmosphere and heated for seven hours at $+10°$ C. to $+100°$ C. The polymer obtained from the reaction is dissolved in benzene and precipitated with odorless mineral spirit. The formation of the block copolymer is demonstrated by the "demixing test similar to those of Hughes and Brown (4) and Molau (5): (4) L. J. Hughes and G. L. Brown, J. Appl. Polymer Sci. 7–59 (1963); (5) G. E. Molau, J. Polymer Sci A3-1267 (1965). The control is a 50/50 mixture of 40% polystyrene and 40% solution of a monohydroxyl terminated polyether (Carbowax-750) in chloroform solution. After these were well mixed the demixing time was 30 minutes. A 40% solution of the block prepared in chloroform showed no demixing in 22.5 hours.

A mixture of 1:1:1 of 40% solutions of polystyrene, Carbowax-750 and the prepared block in chloroform after they were well mixed showed a demixing time of 90 minutes.

EXAMPLE IX

Preparation of block copolymers with styrene from product obtained in Example V

Polystyrene-Polybutadiene

To 15 g. of styrene placed in a tube is added 5 g. of the product obtained on Example V. The tube is sealed under a nitrogen atmosphere and heated for seven hours at $+70°$ C. to $+100°$ C. The polymer obtained from the reaction is dissolved in benzene and precipitated with odorless mineral spirit. The polymer is dried in a vacuum oven for sixteen hours at $+50°$ C. and tested by the demixing test. (4)-(5).

The control is a 50/50 mixture of 15% polystyrene and 15% hydroxyl terminated polybutadiene in benzene solution. After these are well mixed, a demixing time of twenty minutes was obtained. A 15% solution of the block copolymer showed no demixing in 13 days. A mixture of 1:1:1 of 15% solutions of polystyrene, hydroxyl terminated polybutadiene and the block copolymer in benzene gave a demixing time of 6 hours.

EXAMPLE X

Reaction of hydroxy-terminated polybutadiene-styrene with t-butyl o-(chloroformyl) peroxybenzoate

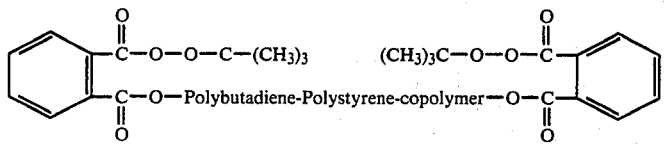

To a solution of 17.6 g. of hydroxyl-terminated polybutadiene polystyrene copolymer (Sinclair C-S-15 resin, equivalent weight 1330) containing 0.75 meq/gm) and triethylamine (1.4 g., 0.0132 moles) in diethyl ether was added a solution of t-butyl o-(chloroformyl) peroxybenzoate (0.0132 moles) in benzene.

After filtration of triethylamine hydrochloride and evaporation of the solvent a viscous liquid was obtained (16 g.) that contained 0.43 A(O).

EXAMPLE XI

Preparation of block copolymer with acrylonitrile from the copolymer containing peroxide in Example X Polybutadiene-Polystyrene-Polyacrylonitrile Into a tube was placed 5 g. of the copolymer containing peroxide (Example X) and 60 g. of toluene which is not a solvent for polyacrylonitrile.

The mixture was cooled at 0° C. and 25 g. of acrylonitrile was added. The tube was sealed under nitrogen and it was heated at 100° C. for 27 hours.

A blank was prepared containing 0.5 g of polybutadiene-polystyrene copolymer (Sinclair C-S-15), 2.5 g. acrylonitrile and 6 g. of toluene and it was heated at 100° C. for 27 hours.

After this time the two solutions was cooled down to 23°–25° C. and contrifugated for 4 hours. The blank failed to give any solid while the other sample separated 7 g. of polyacrylonitrile.

The toluene solution after separation of the solid was precipitated with methanol and 12 g. of solid was obtained. The increase weight of the soluble polymer was a proof of the block formation.

What is claimed is:

1. A polymer of the formula $$[(A_{n1}-R-D_{n2})_v P_{n3}]_w Z_{n4}$$

where
(a) $n_1$, $n_2$, $n_3$ and $n_4$ are integers equal to 1 or 2;
(b) v and w are integers equal to 1-100;
(c) A is selected from

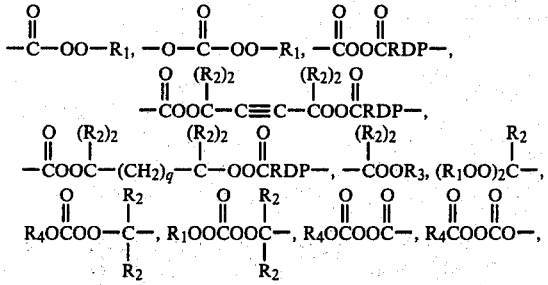

-continued

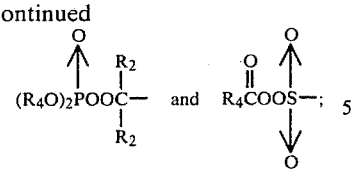

(d) q is an integer equal to 2-4;
(e) D is selected from

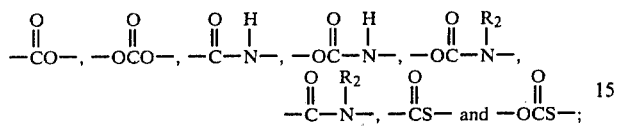

(f) P is a polyvalent residue of a polymer selected from a polyether, polyester, polyamide, polycarbonate, polybutadiene, polystyrene, poly(vinyl alcohol), partially hydrolyzed-poly(vinyl acetate), cellulose and polystyrene-polybutadiene copolymer less its terminal and pendant Z and $(A_{n1}-R-D_{n2})$ grups, with the proviso that P is divalent when A is a diradical or $n_2$ is 2;

(g) Z is selected from —H, —OH, —$NH_2$, —$NHR_2$, —SH, —$OR_2$,

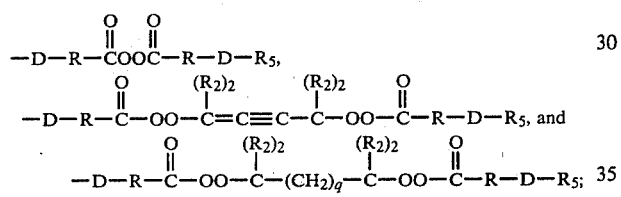

(h) R is a di-, tri- or tetravalent radical selected from alkyl of 1–12 carbons, alkenyl of 2–12 carbons, cycloalkyl of 3–8 carbons, or aryl of 6–12 carbons;
(i) $R_1$ is tertiary alkyl of 4–8 carbons;
(j) $R_2$ is alkyl of 1–12 carbons;
(k) $R_3$ is selected from tertiary alkyl of 4–10 carbons and tertiary aralkyl of 9–10 carbons;
(l) $R_4$ is selected from alkyl of 1–12 carbons or aryl of 6–12 carbons; and
(m) $R_5$ is alkyl of 1–4 carbons or hydrogen.

2. The polymer

having an active oxygen content of about 0.30%.
3. The polymer

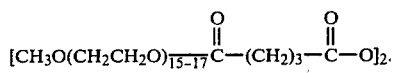

4. A polymer as in claim 1 wherein P is a polyvalent polymeric residue of polybutadiene or polybutadiene-polystyrene copolymer.
5. A polymer as in claim 4 wherein P is a polyvalent polymeric residue of polybutadiene-polystyrene copolymer.
6. A process for preparing peroxy-containing polymers which comprises reacting a polymer containing terminal or pendant acylatable groups with a compound of the formula $$X_n-R_p-Y_m$$

where:
(a) R is an aliphatic, cycloaliphatic or aromatic di-, tri- or tetravalent radical;
(b) p is an integer equal to at least 1;
(c) X is selected from —C(=O)B, —OC(=O)B and —C(=O)OC(=O)—;
(d) B is Cl- or Br-;
(e) Y is selected from —C(=O)OO$R_1$, —C(=O)OOC(=O)R$X_n$, $R_3$OOC($R_2$)($R_2$)—, ($R_1$OO)$_2$C($R_2$)—, $R_4$OC(=O)OOC($R_2$)($R_2$)—, $R_1$OOC(=O)O—, $R_1$OOC(=O)OOC($R_2$)($R_2$)—, $R_4$OC(=O)OOC(=O)—, $R_4$C(=O)OOC(=O)O—, ($R_4$O)$_2$P(→O)OOC($R_2$)($R_2$)—, $R_4$C(=O)OOS(→O)$_2$—, —C(=O)OOC($R_2$)($R_2$)C≡CC($R_2$)($R_2$)OOC(=O)R$X_n$ and —C(=O)OOC($R_2$)($R_2$)—(CH$_2$)$_q$—C($R_2$)($R_2$)OOC(=)R$X_n$;
(f) $R_1$ is tertiary alkyl of 4–8 carbons;
(g) $R_2$ is aliphatic of 1–12 carbons or cycloaliphatic of 3–12 carbons;
(h) $R_3$ is t-alkyl or t-aralkyl of up to 10 carbons;
(i) $R_4$ is aliphatic of 1–12 carbons, cycloaliphatic of 3–12 carbon or aromatic of 6–12 carbons;
(j) n and m are integers equal to 1 or 2; and
(k) q is an integer equal to 2–4;
and recovering peroxy-containing polymer from the resultant reaction mixture.

7. A polymer of the formula $$[(A_{n1}-R-D_{n2})_vP_{n3}]_wZ_{n4}$$

where
(a) $n_1$, $n_2$, $n_3$ and $n_4$ are integers equal to 1 or 2;
(b) v and w are integers equal to 1–100;
(c) A is selected from

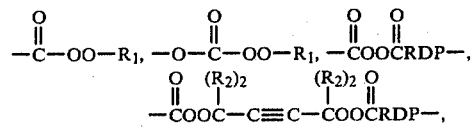

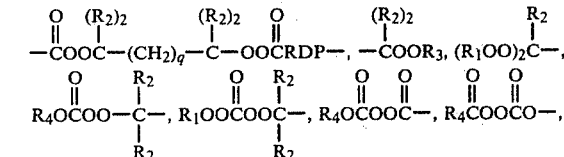

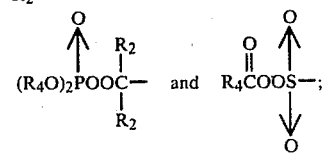

(d) q is an integer equal to 2–4;
(e) D is selected from

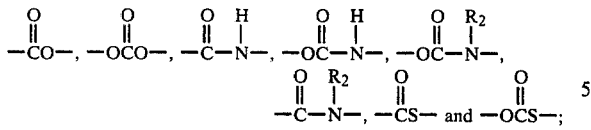

(f) P is a polyvalent residue of polybutadiene less its terminal and pendant Z and $(A_{n1}\text{—}R\text{—}D_{n2})$ groups, with the proviso that P is divalent when A is a diradical or $n_2$ is 2;

(g) Z is selected from —H, —OH, —$NH_2$, —$NHR_2$, —SH, —$OR_2$,

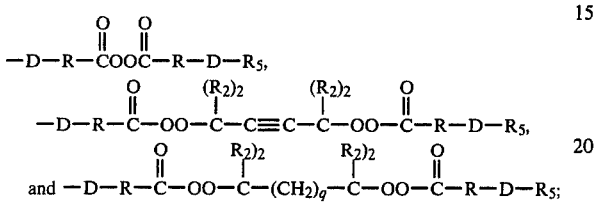

(h) R is a di-, tri- or tetravalent radical selected from alkyl of 1–12 carbons, alkenyl of 2–12 carbons, cycloalkyl of 3–8 carbons, or aryl of 6–12 carbons;

(i) $R_1$ is tertiary alkyl of 4–8 carbons;

(j) $R_2$ is alkyl of 1–12 carbons;

(k) $R_3$ is selected from tertiary alkyl of 4–10 carbons and tertiary aralkyl of 9–10 carbons;

(l) $R_4$ is selected from alkyl of 1–12 carbons or aryl of 6–12 carbons; and (m) $R_5$ is alkyl of 1–4 carbons or hydrogen.

8. A process for preparing peroxy-containing polybutadiene which comprises reacting polybutadiene containing terminal or pendant acylatable groups with a compound of the formula $X_n\text{—}R_p\text{—}Y_m$ where:

(a) R is an aliphatic, cycloaliphatic or aromatic di-, tri- or tetravalent radical;

(b) p is an integer equal to at least 1;

(c) X is selected from —C(=O)B, —OC(=O)B and —C(=O)OC(=O)—;

(d) B is Cl— or Br—;

(e) Y is selected from —C(=O)OO$R_1$, —C(=O)OOC(=O)R$X_n$, $R_3$OOC($R_2$)($R_2$)—, ($R_1$OO)$_2$C($R_2$)—, $R_4$OC(=O)OOC($R_2$)($R_2$)—, $R_1$OOC(=O)O—, $R_1$OOC(=O)OOC($R_2$)($R_2$)—, $R_4$OC(=O)OOC(=O)—, $R_4$C(=O)OOC(=O)O—, ($R_4$O)$_2$P(→O)OOC($R_2$)($R_2$)—, $R_4$C(=O)OOS(→O)$_2$—, —C(=O)OOC($R_2$)($R_2$)C≡CC($R_2$)OOC(=O)R$X_n$ and —C(=O)OOC($R_2$)($R_2$)—(CH$_2$)$_q$—C($R_2$)($R_2$)OOC(=O)R$X_n$;

(f) $R_1$ is tertiary alkyl of 4–8 carbons;

(g) $R_2$ is aliphatic of 1–12 carbons or cycloaliphatic of 3–12 carbons;

(h) $R_3$ is t-alkyl or t-aralkyl of up to 10 carbons;

(i) $R_4$ is aliphatic of 1–12 carbons, cycloaliphatic of 3–12 carbons or aromatic of 6–12 carbons;

(j) n and m are integers equal to 1 or 2; and (k) q is an integer equal to 2–4; and recovering peroxy-containing polybutadiene from the resultant reaction mixture.

9. The process of claim 8 wherein the acylatable groups are hydroxyl, amino or mercapto groups.

* * * * *